United States Patent
Lagodzki et al.

(10) Patent No.: US 10,022,254 B2
(45) Date of Patent: Jul. 17, 2018

(54) POLARIZABLE DELIVERY MECHANISM FOR MEDICAL DEVICE DEPLOYMENT

(71) Applicant: Cook Medical Technologies LLC, Bloomington, IN (US)

(72) Inventors: Karol Lagodzki, Bloomington, IN (US); Jeremy Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 953 days.

(21) Appl. No.: 14/204,236

(22) Filed: Mar. 11, 2014

(65) Prior Publication Data

US 2014/0276540 A1    Sep. 18, 2014

Related U.S. Application Data (60) Provisional application No. 61/781,901, filed on Mar. 14, 2013.

(51) Int. Cl.
    *A61B 17/12*    (2006.01)
    *A61F 2/95*    (2013.01)
    *A61F 2/01*    (2006.01)

(52) U.S. Cl.
    CPC ............ *A61F 2/95* (2013.01); *A61B 17/1214* (2013.01); *A61B 2017/1209* (2013.01); *A61B 2017/12086* (2013.01)

(58) Field of Classification Search
    CPC ...... A61F 2/01; A61F 2/95; A61F 2002/9511; A61F 2002/011; A61F 2/88; A61B 17/12; A61B 2017/1205; A61B 2017/12054; A61B 2017/12063; A61B 2017/12068; A61B 17/12022; A61B 2017/1209; A61B 2017/12086; A61M 37/0069; A61M 25/1018; A61M 2025/1054
    See application file for complete search history.

(56) References Cited

U.S. PATENT DOCUMENTS

| | | | |
|---|---|---|---|
| 4,315,509 A | 2/1982 | Smit | |
| 5,951,566 A | 9/1999 | Lev | |
| 7,618,435 B2 * | 11/2009 | Opolski | ........... A61B 17/12022 606/1 |
| 7,727,269 B2 | 6/2010 | Abraham-Fuchs et al. | |
| 7,771,451 B2 | 8/2010 | Ramzipoor | |
| 8,100,918 B2 | 1/2012 | Gandhi et al. | |
| 2005/0149108 A1 | 7/2005 | Coz | |
| 2008/0027482 A1 | 1/2008 | Sekido et al. | |
| 2009/0177261 A1 | 7/2009 | Teoh et al. | |

(Continued)

*Primary Examiner* — Eric Rosen
*Assistant Examiner* — Mikail Mannan
(74) *Attorney, Agent, or Firm* — Brinks Gilson & Lione (57) ABSTRACT

A delivery device assembly for delivering a medical device to a target site within a patient includes a first polarizable tine and a second reactive tine that is not polarized. The first tine is connected to a first wire that has an electric coil surrounding a portion of the first wire. A current is passed through the electric wire to cause the polarizable tine to become polarized, thereby causing the reactive tine that is not coupled to the electric coil to move toward the polarized tine. The relative movement of the tines releases the medical device from its attachment to the tines.

18 Claims, 4 Drawing Sheets

(56) References Cited

U.S. PATENT DOCUMENTS

2010/0121350 A1\* 5/2010 Mirigian .......... A61B 17/12022
                                                                    606/142
2012/0022633 A1   1/2012 Olson et al.
2012/0283812 A1  11/2012 Lagodzki et al.

\* cited by examiner

POLARIZABLE DELIVERY MECHANISM FOR MEDICAL DEVICE DEPLOYMENT

CROSS-REFERENCE TO RELATED APPLICATIONS

This application claims the benefit under 35 U.S.C. § 119(e) of U.S. Provisional Application No. 61/781,901, filed Mar. 14, 2013, which is hereby incorporated by reference in its entirety.

FIELD

This disclosure relates generally to a mechanism for the deployment of a medical device within a patient. More specifically, this disclosure relates to a delivery assembly for a medical device and a method of mechanically releasing or detaching said device at a targeted vascular site.

BACKGROUND

A standard procedure used in the treatment of endovascular diseases is the placement of medical devices, such as embolic coils, stents, and dilation balloons, among others, at a desired or targeted site (e.g., aneurysm, etc.) within a patient. The delivery of such a medical device has typically been accomplished by a variety of means, including the use of a catheter along with a pushing wire or a means of injection, as well as a system to which the device is attached during delivery and detached once the device is proximate to the targeted site. These medical devices usually have a contracted shape that allows them to pass through the lumen of the body vessel and an expanded shape that occurs after being deployed at the targeted site.

One specific example, of such a medical device is an embolic or occlusive device that is placed within a body vessel or vasculature of the human body to filter the flow of blood through a vessel in the vasculature or to block the flow of blood within a defect in the vessel, such as an aneurysm. One example among many widely accepted types of occlusive devices is a detachable helical wire coil whose coil windings are sized to engage the wall of the vessel. Detachable coils are usually selected when the anatomy is especially distal and tortuous, a risk of coil displacement exists, or a very precise placement of the coil is required.

One example of a detachable medical device delivery device is a pusher member including two polarizable wires that each include a polarizable tine. The two polarizable tines can be polarized to engage a proximal opening of the medical device, or they can be biased into engagement with the medical device. The two tines can then each be polarized such that they are drawn together to release the medical device.

SUMMARY

A system for deploying a medical device is provided, the system comprising: a delivery mechanism including a pusher element having a body portion with a proximal end and a distal end; a first wire coupled to the pusher element and including a first tine extending from the distal end of the pusher element; a second wire coupled to the pusher element and including a second tine extending from the distal end of the pusher element; a medical device having a proximal part and a distal part, wherein the proximal part is detachably attached to the first and second tines; a polarizing device operatively connected to the first wire but not the second wire, wherein the polarizing device causes the first wire and first tine to become polarized when activated; and wherein the first tine has a polarized state and an unpolarized state, and the second tine is drawn toward the first tine when the first tine is in the polarized state.

In another form, a polarizable delivery device for a medical device is provided, the delivery device comprising: a first wire having a proximal end and a distal end and including a first tine at the distal end; a second wire extending along the first wire, the second wire having a proximal end and a distal end and including a second tine at the distal end; an electric coil surrounding a portion of the first wire and not surrounding any portion of the second wire, wherein the electric coil is capable of producing an electric current therethrough that creates a polarized condition of the first wire but does not polarize the second wire; wherein the first tine and second tine are biased outward when current is not running through the electric coil and the first wire is not polarized; and wherein the first tine and second tine move relatively toward each other when current is running through the electric coil and the first wire is polarized by the electric coil.

In another form, a method for delivering a medical device, the method comprising: inserting toward a target site within a patient's body a medical device assembly including a medical device detachably attached to a polarizable delivery mechanism, wherein the polarizable delivery mechanism comprises: a first wire having a proximal end and a distal end and including a first tine at the distal end, the first tine attached to the medical device; a second wire extending along the first wire, the second wire having a proximal end and a distal end and including a second tine at the distal end, the second tine attached to the medical device; and a polarizing device operatively coupled to a portion of the first wire and not coupled to any portion of the second wire; activating the polarizing device to polarize the first wire but not the second wire; in response to polarizing the first wire but not the second wire, attracting the second tine toward the first tine; and in response to attracting the second tine toward the first tine, detaching the medical device from the polarizable delivery mechanism.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. One skilled-in-the-art will understand that a helical coil is used in the Figures as an example of a medical device and that other medical devices may be utilized without exceeding the scope of the disclosure.

DETAILED DESCRIPTION

The following description is merely exemplary in nature and is in no way intended to limit the present disclosure or its application or uses. It should be understood that throughout the description and drawings, corresponding reference numerals indicate like or corresponding parts and features.

The present disclosure generally provides a medical device assembly that includes a polarizable delivery mechanism for the deployment of a medical device at a targeted site in a body vessel or vasculature of a patient, as well as a method of using said delivery mechanism. The polarizable delivery mechanism basically comprises a pusher element, such as a guide wire, having a proximal end and a distal end. The distal end of the pusher element has two tines adapted to reversibly interact with a medical device to either hold or release said device in an engaged or detached position, respectively. The polarizable delivery mechanism has an engaged position in which the tines make contact with the inner wall of an opening in the medical device to securely hold the device during deployment. The opening in the medical device may be part of a bracket, ring, or other feature on the medical device designed to interact with the tines of the pusher element. The medical device may be attached proximate to the distal end of the pusher element during the manufacturing process or by the attending operator prior to performing the deployment procedure by placing the tines of the distal section of the pusher element into the opening in the medical device such that the medical device is releasably held by the polarizable delivery mechanism.

In use, the pusher element, with the medical device attached, is advanced through a catheter to a targeted vascular site in a patient. Upon exiting the distal end of the catheter, the polarizable delivery mechanism is made to undergo a transition from an engaged position to a detached position, in which the tines of the pusher element no longer engage the medical device, thereby, allowing the medical device to be released and/or deployed. The pusher element can then be withdrawn, leaving the medical device in the desired position. Thus, the polarizable delivery mechanism of the present disclosure does not automatically release the medical device when it is extruded from the catheter, but rather, requires the action of the operator to initiate the mechanism to switch from the coupled or engaged position to its detached or unengaged position. Only one of the tines is coupled to a polarizing device to cause the tine to become polarized. The other tine will react to the polarization of the polarized tine and be drawn toward it.

Figure 1A:
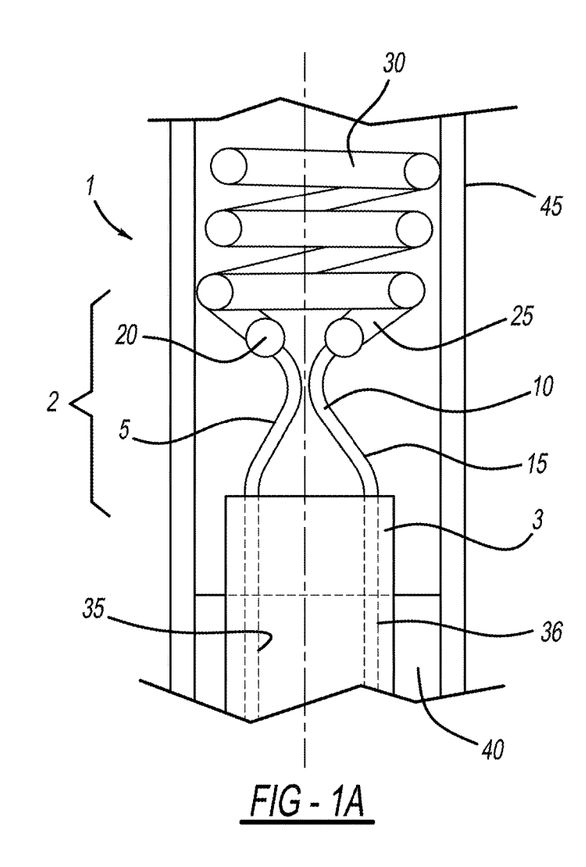
FIG. 1A is a schematic view of a polarizable delivery mechanism in an engaged position.

Referring to FIG. 1A, the medical device assembly 1 includes a polarizable delivery mechanism 2 that comprises a pusher element 3 defined by a proximal and distal end with a first tine 5 configured to be polarized and a second tine 10 configured to be attracted to the polarized tine 5 but remaining free from being polarized itself. The tines 5, 10 are located at the distal end of the pusher element 3. Each of the tines 5, 10 also are defined by a proximal section 5a, 10a and a distal section 5b, 10b. The proximal section 5a, 10a is in contact with the distal end of the pusher element 3, while the distal section 5b, 10b of the tines is capable of interacting with a bracket or other mechanism 25 located on the proximal part of a medical device 30.

Figure 2:
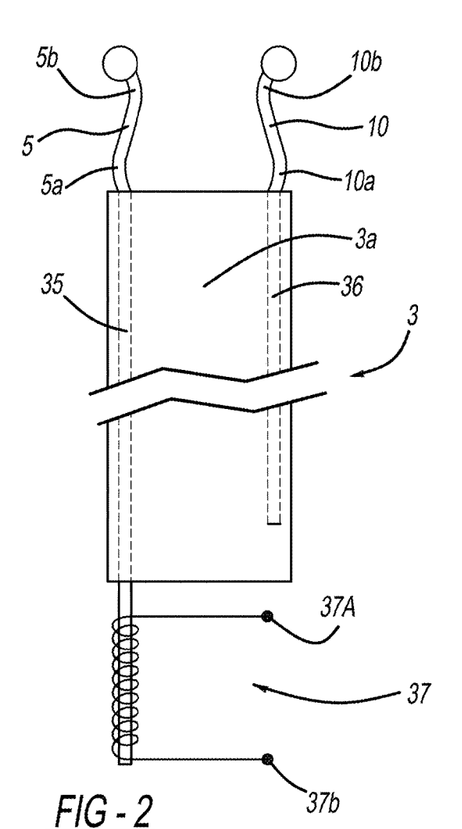
FIG. 2 is a schematic view of a pusher member of the polarizable delivery system.

With reference to FIG. 2, the proximal sections 5a and 10a of the tines 5, 10 can extend from the distal ends of wires 35, 36 extending through the pusher element 3. In one form, the tine 5 and first wire 35 are formed as one piece, as are the tine 10 and second wire 36. The active tine 5 may become activated via the application of an energy stimulus travelling through the first wire 35 incorporated into the pusher element 3 for that specific purpose.

The active tine 5 and first wire 35 may be made of any material that can be polarized, and the reactive tine 10 and second wire 36 can be made of any material that will be drawn toward a polarized material, such that movement of the tines 5, 10 relative to each other can thereby be induced. Several examples of materials that can be magnetically polarized and or attracted toward a magnetically polarized material include, but are not limited to, ferromagnetic metals and metal alloys comprising iron (Fe), nickel (Ni), cobalt (Co), gadolinium (Gd), and mixtures or combinations thereof.

In the case where the energy stimulus is a magnetic field, the magnetic field can be generated by applying an electric current to an electric coil 37 located somewhere along the path of the first wire 35 that includes the active tine 5 at its distal end, even at the proximal end of the first wire 35 located outside the body vessel or vasculature 45 of the patient. In one form, the electric coil 37 can be wound around the proximal end of the first wire 35, as shown in FIG. 2, with a first lead 37a extending from one end of the coil 37 and a second lead 37b extending from the opposite end of the electric coil 37. The leads 37a, 37b can be coupled to a power source or other electric current generator (not shown) that can generate a current through the electric coil 37. The electric coil 37 can be made of copper or another generally highly conductive material. The number, size, and spacing of the coils defining the electric coil 37 can vary depending on the needs of the user.

If the lead 37a is positive, then lead 37b is negative; if the lead 37b is negative, then the lead 37a is positive. Depending on the direction of the current generated by the coil 37, the active tine 5 will have either a north or south polarity, as known in the art. The active tine 5, being activated and having one of these polarities, will create a magnetic field. The reactive tine 10 will react to the magnetic field generated by the active tine 5 and the two tines will be drawn together. While the electric coil 37 has been described, other polarizing devices can also be used that are capable of being coupled to the first wire 35 but not the second wire 36 in order to polarize just the first wire 35 including the active tine 5 to thereby cause the reactive tine 10 to be drawn toward the active 5.

Figure 3:
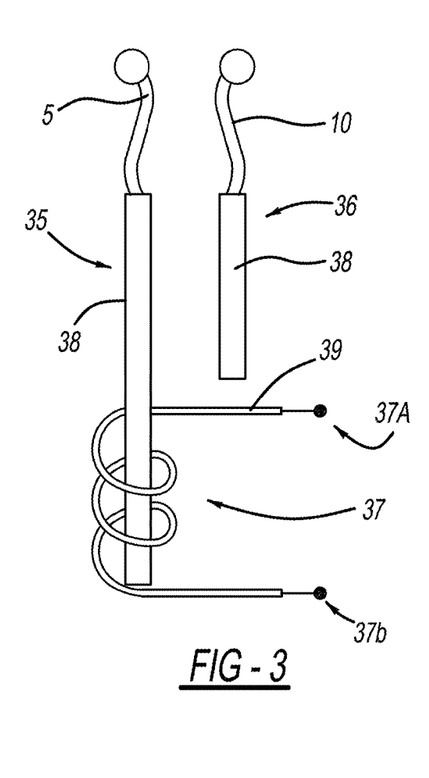
FIG. 3 is a schematic view of a first and second wire and an electric coil of the polarizable delivery mechanism.

With reference to FIG. 3, the electric coil 37, and wires 35, 36, can each be insulated from each other so that current is not transmitted from one component to another through direct contact. In one form, the first wire 35 includes an insulation layer 38 extending along at least a portion of its length. The insulation layer 38 can be made of a polymer material that will generally not transmit current, such as polyurethane, nylon, or the like. The insulation layer 38 can have any thickness suitable to insulate the first wire 35. Similarly, the second wire 36 can likewise include the insulation layer 38. However, the second wire 36 can also remain free from an insulation layer if the second wire 36 is not in contact with an electric coil.

The electric coil 37, which surrounds a portion of the first wire 35, may also be insulated using an insulation layer 39 similar to layer 38, or a space can be maintained between the electric coil 37 and the first wire 35. If the coil 37 is insulated, either through spacing or the insulation layer 39, then the first wire 35 could be free from insulation, as current would not be transmitted to the first wire 35 due to the insulation of the electric coil 37. If an insulation layer 38 is applied to the first wire 35, or an insulation layer 39 is applied to the coil 37, the first wire 35 and coil 37 can contact each other without transferring current therebetween.

With reference again to FIG. 2, the wires 35 and 36 can extend longitudinally through a body 3a of the pusher element 3, which can provide both support and insulation to the wires 35 and 36. In one form, the second wire 36 can extend partially through the body 3a of the pusher element. The first wire 35 can extend proximally from the proximal end of the pusher element 3, where the electric coil 37 can spiral around the exposed portion of the first wire 35. The electric coil 37 can then be easily attached to the power source or current generating device. The second wire 36, which is not polarized, can remain within the body of the pusher element 3, as it does not need to be coupled with any polarizing structure. Thus, this arrangement using a single active tine 5 that can be polarized provides a cheaper, simpler, and easy to manufacture solution relative to systems using multiple polarized wires. In another form, the second wire 36 that includes the reactive tine 10 could merely extend from the distal end of the pusher element 3 to provide the reactive tine 10 adjacent the active tine 5. Because the reactive tine 10 is not polarized by any polarizing device, it does not need to extend through the pusher element 3 to be connected to a polarizing device.

Figure 1B:
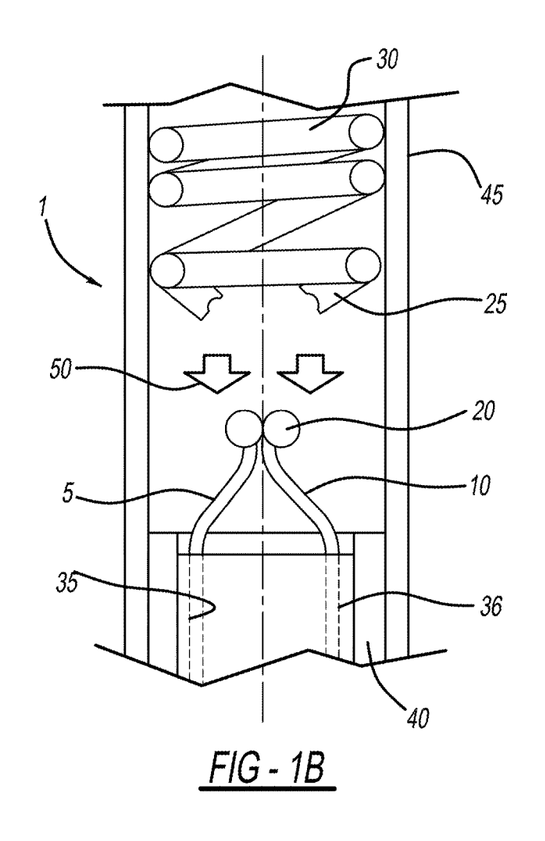
FIG. 1B is a schematic view of the polarizable delivery mechanism of FIG. 1A shown in a detached position.

Referring back to FIG. 1A, according to one aspect of the present disclosure, the tines 5, 10 are positioned to interact with the bracket 25 of the medical device 30 in an inactive state. This inactive state includes the active tine 5 not being polarized and the reactive tine 10 not being drawn toward a magnetic field generated by the active tine 5. The tines 5, 10 can sized or shaped in a manner known in the art to bias the tines 5, 10 outwardly toward the bracket 25 to secure the medical device 30 when in this inactive state. The pusher element 3 with the polarizable delivery mechanism 2 in its engage position pushes the medical device 30 through a catheter 40 positioned within the vasculature 45 of a patient. The medical device 30 in contact with the tines 5, 10 of the pusher element 3 exits the end of the catheter 40. Once located at the targeted site in the vasculature 45, the medical device 30 may be detached from the pusher element 3 as shown in FIG. 1B.

The ends of the tines 5, 10 in the distal section 5b, 10b of each tine 5, 10 are represented in FIGS. 1A-3 as circular balls. However, one skilled in the art will understand that these ends can be any shape capable of reversibly engaging the bracket 25 of the medical device 30 without exceeding the scope of the present disclosure. Similarly, the bracket 25 on the proximal part of the medical device 30 may be any shape known to one skilled in the art capable of reversibly engaging the tines 5, 10 of the polarizable delivery mechanism 2.

Figure 4A:
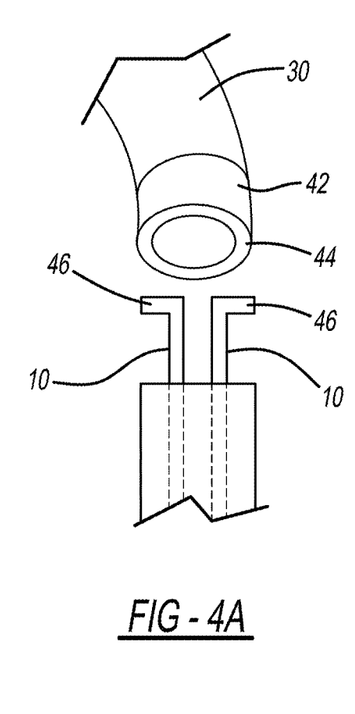
FIG. 4A is a schematic view of another embodiment of a connection between a delivery mechanism and a medical device, illustrating a detached configuration.

For example, and with reference to FIG. 4A, one type of connection can be in the form of an attachment ring 42 that is disposed at the proximal end of the medical device 30. The attachment ring 42 can extend radially inward to create a ledge 44. The tines 5, 10 can include outwardly extending finger portions 46 that can be disposed distally past the ledge 44 to retain the medical device 30 in an engaged position. When the tines 5, 10 move relatively toward each other when active tine 5 is polarized to disengage the medical device 30, the fingers 46 will disengage the ring 42, freeing the medical device 30.

Figure 4B:
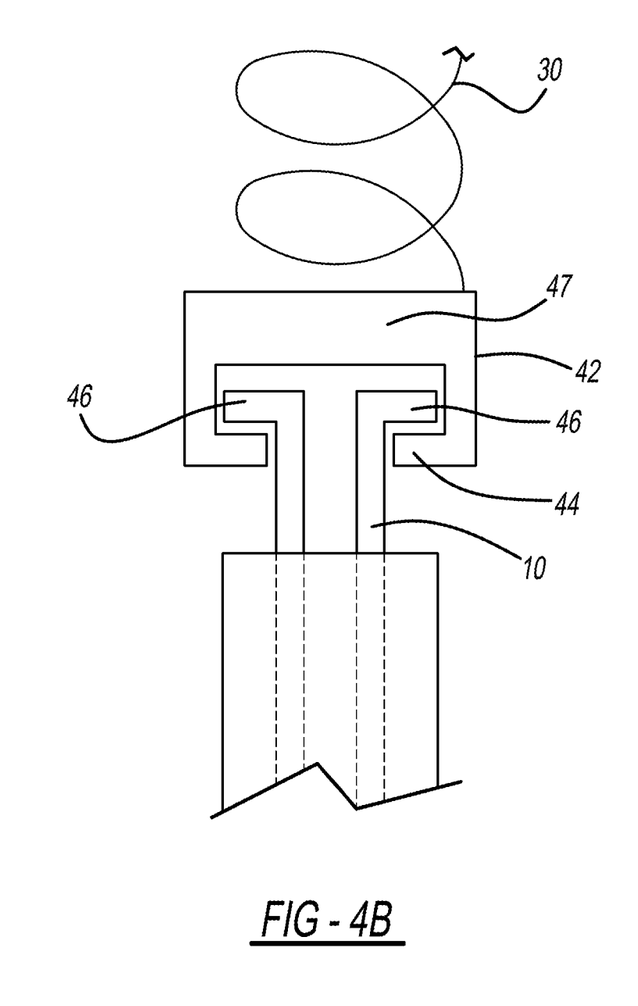
FIG. 4B is a schematic view of another embodiment of a connection between a delivery mechanism and a medical device, illustrating an attached configuration.

In another form, and with reference to FIG. 4B, another type of connection similar to the connection shown in FIG. 4A includes a wall portion 47 extending across the attachment ring 42 and disposed between the ledge 44 and the medical device 30. The wall portion 47 can provide additional control while delivering the medical device 30 by allowing the tines 5, 10 to push against the wall portion 47 to advance the medical device 30. Similar to the above, when the tines 5, 10 move relatively toward each other, the when active tine 5 is polarized to disengage the medical device 30, the fingers 46 will disengage the ring 42, and the tines 5, 10 can be retracted away from the wall portion 47, freeing the medical device 30.

Referring now to FIG. 1B, the medical device 30 is detached from the tines 5, 10. The polarization of the active tine 5 may occur by the application of an energy stimulus through the electric coil 37, which magnetizes the first wire 35 having the active tine 5 at its distal end. Once polarized, the active tine 5 will attract the reactive tine 10 as described above, thereby moving the tine 5 and 10 towards one another, overcoming their outward bias, and losing contact with the bracket 25 of the medical device 30. The lack of contact between the tines 5, 10 and the bracket 25 allows the medical device 30 to become detached from the pusher element 3. Upon becoming detached from the medical device 30, the pusher element 3 may be withdrawn 50 from the vasculature 45 of the patient.

In order to demonstrate the polarization of the tines 5, 10, the mechanism of polarization is described in FIGS. 1-4 as being magnetic in nature. However, one skilled in the art will understand that other polarization devices or mechanisms may be used without exceeding the scope of the present disclosure, provided such polarization mechanisms are capable of causing the tines 5, 10 to move relative to one another in response to polarizing the active tine 5 to detach the tines 5, 10 from a medical device 30.

The polarizable delivery mechanism 2 of the medical device assembly 1 has two positions relative to the medical device 30. These positions are, namely, an attached or engaged position and a detached position. In the engaged position, the tines 5, 10 of polarizable delivery mechanism 2 engage the bracket 25 or ring 40 of the medical device 30 and allows the pusher element 3 to move the polarizable delivery mechanism 2 and medical device 30 together as a medical device assembly 1, even after the medical device 30 is extruded from the end of the delivery catheter 40. In the detached position, the polarizable delivery mechanism 2 does not engage the medical device 30 and the medical device 30 is released or deployed at the selected target site in the vasculature 45 of the patient.

The medical device assembly 1 is designed such that the default position for the polarizable delivery mechanism 2 is the engaged position. The switching between the engaged and detached positions is controlled by an operator, such as a physician or surgeon, through the application of an energy stimulus, such as an electric current applied to the electric coil 37 or other means to induce the polarization of the active tine 5.

The polarizable delivery mechanism 2 as described herein can be adapted to be used with a variety of medical devices 30, including, but not limited to, embolic protection devices, occlusive devices, stents, and dilation balloons, among others. The medical device 30 may comprise any structure known to one skilled-in-the-art, including for example, occlusive devices of tubular structures, having braids, coils, a combination of braids and coils, or the like. The occlusive device may change shape during deployment, such as changing from a collapsed configuration to an expanded configuration. One example, among many examples, of a medical device 30 used with the polarizable delivery mechanism 2 to form the medical device assembly 1 of the present disclosure is a Nester® embolization coil (Cook Medical Incorporated, Bloomington, Ind.).

The delivery catheter 40 used to deliver the medical device 30 may be made of any material known to one skilled-in-the-art. Such material may include but not be limited a polyimide, polyether amide, nylon, polytetrafluoroethylene (PTFE), polyetheretherketone (PEEK), and mixtures or copolymers thereof. In its basic form, the catheter is a hollow elongated tube sized to receive the medical device 30 attached to the polarizable delivery mechanism 2. The length of the delivery catheter 40 may be any length necessary or desired to deploy the medical device 30 at the targeted site in the body vessel or vasculature 45 of a patient.

Another objective of the present disclosure is to provide a method of deploying a medical device 30 at a targeted site in the vasculature of a patient. This method generally comprises the steps of introducing the medical device assembly 1 described herein into the vasculature 45 of the patient, wherein the polarizable delivery mechanism 2 of the medical device assembly 1 is in its engaged position with the medical device 30; and then switching the polarizable delivery mechanism 2 to its detached position, thereby, deploying the medical device 30 at the targeted or desired site.

Figure 5:
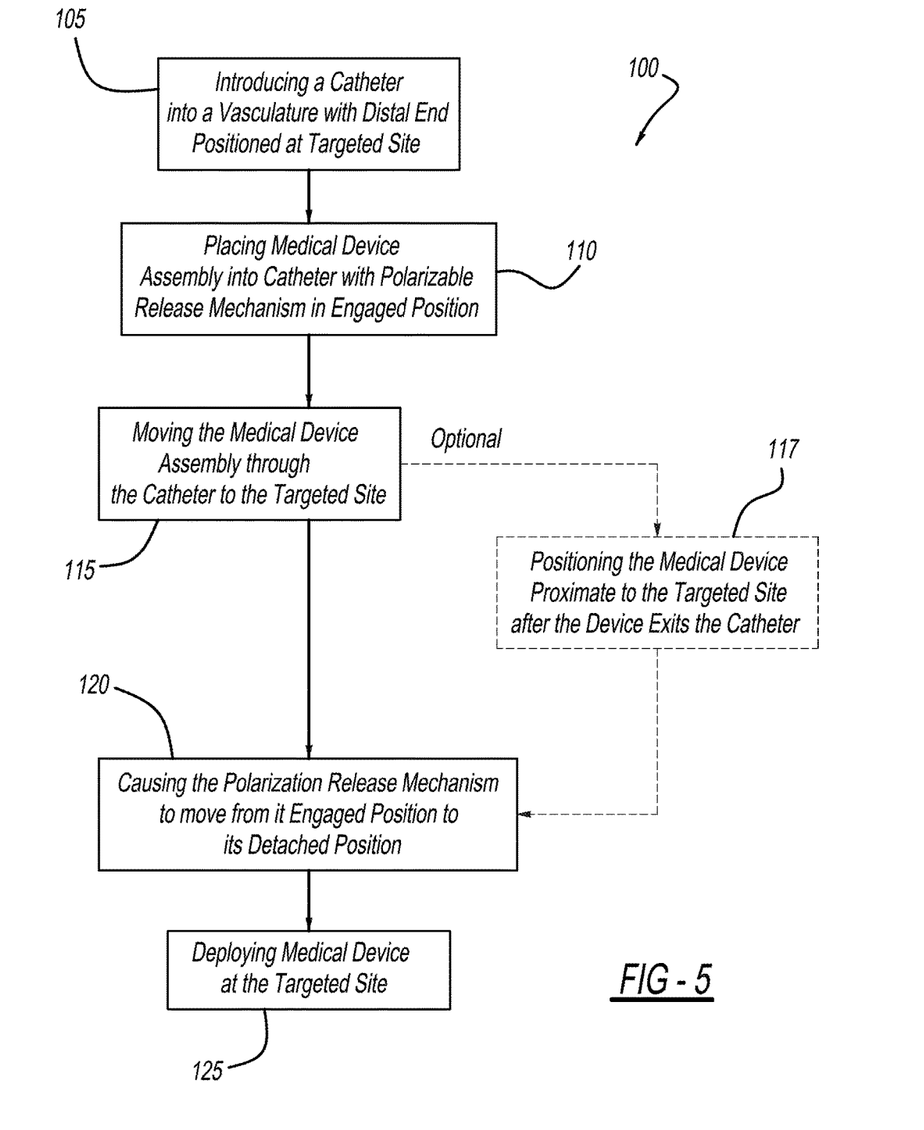
FIG. 5 is a schematic representation of a method of deploying a medical device into a vasculature of a patient using a medical device assembly having polarizable delivery mechanism made according to the teachings of the present disclosure.

FIG. 5 depicts an example of a method 100 used to deploy a medical device 30 to a targeted or desired site in the vasculature 45 of a patient. This method 100 generally comprises introducing 105 a catheter 40 into the vasculature 45 of a patient and positioning the distal end of said catheter 40 at a desired or targeted site. A medical device assembly 1 including the aforementioned medical device 30 and polarizable delivery mechanism 2 is then placed 110 into the catheter 40. At this time, the polarizable delivery mechanism 2 is in its engaged position and securely holds the medical device 30 in a detachably attached configuration. The pusher element 3 having the first wire 35 and the second wire 36 is then allowed to move 115 the medical device assembly 1 through the catheter 40 to the targeted site. Optionally, the operator may further position 117 the medical device 30 proximate to the targeted site after the device 30 exits the catheter 40. The operator then causes the polarizable delivery mechanism 2 to move 120 from its attached or engaged position to its detached position. More specifically, the operator can polarize the first wire 35 by activating the polarizing device or electric coil 37 by running a current through the coil. The active tine 5 at the end of the first wire 35 will be polarized, and the reactive tine 10 will move toward the active tine 5. The polarizable delivery mechanism 2 thus transitions from the engaged position to the detached position. This operator action causes the tines 5, 10 to move relatively toward each other such that contact between the tines 5, 10 and the medical device 30 is reduced, thereby allowing the medical device 30 to be deployed 125 into the vessel or vasculature 45 of the patient at the targeted site.

The present disclosure provides a polarizable delivery mechanism 3 that securely holds a medical device 30 during the deployment of the medical device 30. The polarizable delivery mechanism 2 also allows for the easy and reliable detachment of the medical device 30 once the device 30 is properly positioned proximate to the targeted site. The polarizable delivery mechanism 2 of the present disclosure provides the operator (e.g., interventionalist, etc.) with improved control over the medical device 30 during its deployment, and allows the operator to position and even reposition the medical device 30 at the targeted site in the vasculature 45 of a patient before detachment. One skilled in the art will understand that the polarizable delivery mechanism 2 of the present disclosure is readily adaptable for use with a wide variety of medical devices 30.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

As a person skilled in the art will readily appreciate, the above description is meant as an illustration of implementation of the principles this invention. This description is not intended to limit the scope or application of this invention in that the invention is susceptible to modification, variation, and change, without departing from the spirit of this invention, as defined in the following claims.

What is claimed is:

1. A system for deploying a medical device, the system comprising:
    a delivery mechanism including a pusher element having a body portion with a proximal end and a distal end;
    a first wire coupled to the pusher element and including a first tine extending from the distal end of the pusher element;
    a second wire coupled to the pusher element and including a second tine extending from the distal end of the pusher element;
    a medical device having a proximal part and a distal part, wherein the proximal part is detachably attached to the first and second tines;
    a polarizing device operatively connected to the first wire but not the second wire, wherein the polarizing device causes the first wire and first tine to become polarized when activated; and
    wherein the first tine has a polarized state and an unpolarized state, and the second tine is drawn toward the first tine when the first tine is in the polarized state, wherein an extended portion of the first wire extends proximally from the proximal end of the pusher element and the polarizing device is operably connected to the extended portion of the first wire.

2. The system of claim 1, wherein the first tine and second tine are biased outwardly with the medical device attached thereto.

3. The system of claim 1, wherein the first tine and second tine move inwardly to detach the medical device when the first tine is polarized.

4. The system of claim 1, wherein the proximal portion of the medical device comprises an attachment ring.

5. The system of claim 4, wherein the attachment ring includes an inwardly extending ledge portion and a wall portion, and the first tine and the second tine each include outwardly extending finger portions that engage the attachment ring between the ledge portion and the wall portion to attach the medical device.

6. The system of claim 1, wherein the polarizing device is insulated from the first wire.

7. The system of claim 6, wherein the polarizing device includes an insulation layer to insulate it from the first wire.

8. The system of claim 6, wherein the first wire includes an insulation layer to insulate it from the polarizing device.

9. The system of claim 6, wherein the first wire and the polarizing element define an empty space therebetween, and the first wire and polarizing device do not contact each other to insulate the first wire from the polarizing device.

10. The system of claim 1, wherein the second wire is insulated from the first wire.

11. The system of claim 10, wherein the second wire includes an insulation layer to insulate it from the first wire.

12. A system for deploying a medical device, the system comprising:
a delivery mechanism including a pusher element having a body portion with a proximal end and a distal end;
a first wire coupled to the pusher element and including a first tine extending from the distal end of the pusher element;
a second wire coupled to the pusher element and including a second tine extending from the distal end of the pusher element;
a medical device having a proximal part and a distal part, wherein the proximal part is detachably attached to the first and second tines;
a polarizing device operatively connected to the first wire but not the second wire, wherein the polarizing device causes the first wire and first tine to become polarized when activated; and
wherein the first tine has a polarized state and an unpolarized state, and the second tine is drawn toward the first tine when the first tine is in the polarized state;
wherein the polarizing device is an electric coil coiled around a portion of the first wire.

13. The system of claim 12, wherein the electric coil includes a first end and a second end, one of the first end and the second end has a positive charge, and the other has a negative charge.

14. A polarizable delivery device for a medical device, the delivery device comprising:
a first wire having a proximal end and a distal end and including a first tine at the distal end;
a second wire extending along the first wire, the second wire having a proximal end and a distal end and including a second tine at the distal end;
an electric coil surrounding a portion of the first wire and not surrounding any portion of the second wire, wherein the electric coil is capable of producing an electric current therethrough that creates a polarized condition of the first wire but does not polarize the second wire;
wherein the first tine and second tine are biased outward when current is not running through the electric coil and the first wire is not polarized; and
wherein the first tine and second tine move relatively toward each other when current is running through the electric coil and the first wire is polarized by the electric coil.

15. The delivery device of claim 14, wherein the first wire and second wire each extend partially through and are supported by a pusher element, the first tine and second tine extend distally from a distal end of the pusher element, the first wire extends proximally from a proximal end of the pusher element, and the electric coil surrounds the first wire at its proximal end.

16. A method for delivering a medical device, the method comprising:
inserting toward a target site within a patient's body a medical device assembly including a medical device detachably attached to a polarizable delivery mechanism, wherein the polarizable delivery mechanism comprises:
a first wire having a proximal end and a distal end and including a first tine at the distal end, the first tine attached to the medical device;
a second wire extending along the first wire, the second wire having a proximal end and a distal end and including a second tine at the distal end, the second tine attached to the medical device; and
a polarizing device operatively coupled to a portion of the first wire and not coupled to any portion of the second wire, wherein the polarizing device comprises an electric coil surrounding a portion of the first wire;
activating the polarizing device to polarize the first wire but not the second wire, the step of activating the polarizing device comprising applying a current through the electric coil to polarize the first wire;
in response to polarizing the first wire but not the second wire, attracting the second tine toward the first tine; and
in response to attracting the second tine toward the first tine, detaching the medical device from the polarizable delivery mechanism.

17. The method of claim 16 further comprising overcoming an outward bias of the first and second tine to detach the medical device.

18. The method of claim 16, wherein the electric coil surrounds a proximal portion of the first wire and does not surround any portion of the second wire.

* * * * *